United States Patent [19]

Haugwitz et al.

[11] Patent Number: 5,157,049
[45] Date of Patent: Oct. 20, 1992

[54] METHOD OF TREATING CANCERS SENSITIVE TO TREATMENT WITH WATER SOLUBLE DERIVATIVES OF TAXOL

[75] Inventors: Rudiger D. Haugwitz, Bethesda, Md.; Leon Zalkow, Atlanta, Ga.; Jan Glinski, Ridgefield, Conn.; Mathew Suffness, Silver Spring, Md.; Howard M. Deutsch, Atlanta, Ga.; Venkatachala Narayanan, Gaithersburg, Md.

[73] Assignee: The United States of America as represented by the Department of Health & Human Services, Washington, D.C.

[21] Appl. No.: 784,624

[22] Filed: Oct. 31, 1991

Related U.S. Application Data

[60] Continuation of Ser. No. 520,407, May 8, 1990, abandoned, which is a division of Ser. No. 165,173, Mar. 7, 1988, Pat. No. 4,942,184.

[51] Int. Cl.$^5$ .................. A61K 31/335; A61K 31/54; A61K 31/535; A61K 31/495; A61K 31/445; A61K 31/40
[52] U.S. Cl. .................. 514/449; 514/228.2; 514/232.8; 514/253; 514/320; 514/422; 514/450
[58] Field of Search .................. 514/227.8, 233.8, 255, 514/422, 449, 450, 228.2, 232.8, 253, 320

[56] References Cited

PUBLICATIONS

Annual Report to the Food and Drug Administration, Taxol, Ind 22850, Mar. 1991 (National Cancer Institute).
Donehower et al. Cancer Treatment Reports 71(12), 1171–1177, 1987.
Rowinsky et al. Cancer Research 49, 4640–4647 1989.

*Primary Examiner*—Jerome D. Goldberg
*Attorney, Agent, or Firm*—Robert Benson

[57] ABSTRACT

The invention involves the treatment of cancer in humans by administering water soluble derivatives of taxol. The types of cancer so treatable are those sensitive to treatment with taxol.

7 Claims, No Drawings

METHOD OF TREATING CANCERS SENSITIVE TO TREATMENT WITH WATER SOLUBLE DERIVATIVES OF TAXOL

This application is a continuation of application Ser. No. 07/520,407 filed May. 8, 1990, now abandoned, which is a divisional application of Ser. No. 07/165,173, filed Mar. 7, 1988, now U.S. Pat. No. 4,942,184.

BACKGROUND OF THE INVENTION

1. Technical Field

The present invention is related to new, water soluble derivatives of taxol with antineoplastic activity. More particularly, the present invention is related to 2'-O-acyl derivatives of taxol with improved water solubility while retaining antineoplasic property of the parent compound and methods of preparing the same.

2. State of the Art

The diterpene taxol was first isolated in 1971 from the Western Yew, *Taxus brevifolia* Nut by Wani et al (*J. Amer. Chem. Soc.* 46:1469, 1981), who established its structure by chemical and X-ray crystallographic methods. Numerous studies have indicated that taxol and various taxane derivatives are highly cytotoxic and possess strong in vivo activity in a number of test systems. The mechanism of action of taxol has been extensively studied and is summarized by Horwitz (*Pharmacol. Ther.* 25:83, 1984). Briefly, taxol is a unique antimitotic agent which acts by promoting tubulin assembly into stable aggregated structures which resist depolymerization by dilution, calcium ion, cold, and a number of microtubule-disrupting drugs. The formulation of taxol for antitumor testing has been difficult due to its extremely low aqueous solubility, and lack of functional groups that would allow salt formation.

SUMMARY OF THE INVENTION

It is, therefore, an object of the present invention to provide taxol derivatives with improved water solubility while retaining the cytotoxic properties of the parent compound.

It is a further object of the present invention to provide methods for synthesizing water soluble derivatives of taxol with antineoplastic activity.

It is another object of the present invention to provide a method of treating cancer by water soluble derivatives of taxol, wherein said cancer is sensitive to said treatment.

Other objects and advantages will become evident from the Detailed Description of the Invention.

DETAILED DESCRIPTION OF THE INVENTION

The above and various other objects and advantages of the present invention are achieved by water soluble taxol derivatives having the following general formula:

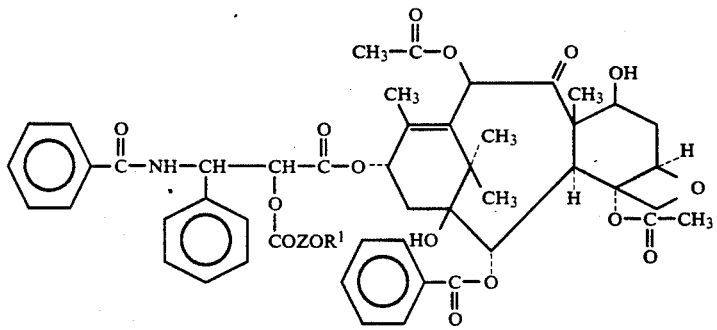

Wherein:
Z = ethylene, propylene, CHCH, 1,2-cyclohexane, 1,2-phenylene,
$R^1$ = OH base, $NR^2R^3$, $OR^3$, $SR^3$, $OCH_2CONR^4R^5$, OH
$R^2$ = hydrogen, methyl
$R^3$ = $(CH_2)_nNR^6R^7$; $(CH_2)_nNR^{\oplus 6}R^7R^8X^{\ominus}$
n = 1 to 3
$R^4$ = hydrogen, lower alkyl containing 1 to 4 carbons
$R^5$ = hydrogen, lower alkyl containing 1 to 4 carbons, benzyl, hydroxyethyl, $CH_2CO_2H$, dimethylaminoethyl
$R^6R^7$ = lower alkyl containing 1 or 2 carbons, benzyl or $R^6$ and $R^7$ together with the nitrogen atom of $NR^6R^7$ form the following rings

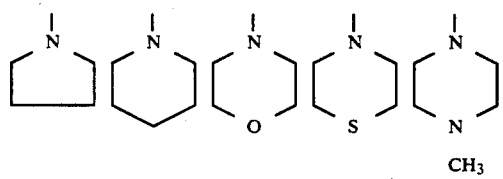

$R^8$ = lower alkyl containing 1 or 2 carbons, benzyl
$X^{\ominus}$ = halide
base = $NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Melting points were determined with Kofler hot stage microscope and corrected. All temperatures are in degrees centigrade. NMR spectra were determined with either a Bruker WM-300 or Varian XL-400 spectrometer, chemical shifts are in ppm relative to TMS (0.00). Mass spectra were recorded on a Varian-Mat 112S or a VG ZAB spectrometer. Preparative centrifugal TLC was done on a Harrison Research Model 7924T (Chromatotron).

These novel derivatives of structure 1 are conveniently synthesized by first acylating taxol 2 with appropriate acid 3 by one of known procedures in which the acid is activated prior to reaction with taxol, involving formation of a symmetric anhydride, mixed anhydride, active ester, acid chloride or the like to yield the taxol acid 4. The activation step can be brought about by various agents, such as carbonyldiimidazole, dicyclohexylcarbodiimide, hydroxybenzotriazole and the like. The addition of pyridine or 4-N,N-dimethylamino-pyridine i.e. DMAP frequently catalyzes the acylation step.

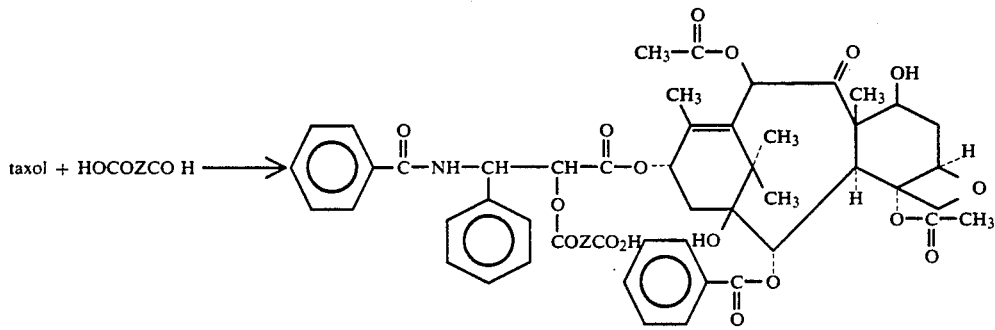

Further reaction conditions for this transformation can be found in such publications as: *Protective Groups in Organic Chemistry*, T. W. Greene, John Wiley & Sons, N.Y., 1981; *Drugs of the Future*, 6:165 (1981); *J. Med. Chem.*, 13:607 (1970); and *Med. Res. Rev.*, 1:189 (1981).

Compounds of structure 4 form physiologically acceptable salts 5 with inorganic and organic bases by the addition of one equivalent of base. These salts frequently provide useful means for isolating the products from reaction mixtures by forming the salt in a medium in which it is insoluble. The free acid may then be obtained by neutralization, e.g., with an acid such as hydrochloric acid. Then any other salt may again be formed from the free acid and the appropriate base. Illustrative are the ammonia salt, alkali salts, and organic amine salts which are preferred. Examples of the organic amine salts include trimethylamine, triethylamine, triethanolamine, N-methyl-N,N-diethanolamine, N-methylglucamine.

Coupling of acids 4 in an activated form, i.e., mixed anhydride, active ester, acid chloride or the like with the appropriate amine, alcohol, thiol or glycolamide yields compounds of structure 1 where R is NR R, OR, SR, or OCH CONR R, respectively. Compounds of structure 1 where R=(CH) NR R R X can be prepared by reacting compounds 1 where R=(CH) NR R with an alkyl halide R X at ambient or elevated temperatures ranging from 50 to about 100 C. for period up to 48 hours. Preferred solvents for the quaternization of the amine are acetonitrile, ethanol or toluene.

The following examples are provided for illustrative purposes only without departing from the spirit or scope of the invention.

EXAMPLE 1

2' Succinyltaxol

After 3 hours at room temperature, a solution of 500 mg (0.59 mmole) of taxol, 900 mg (7.6 mmole) of succinic anhydride in 12 mL of pyridine is evaporated to dryness in vacuo. The residue is treated with 20 mL of water, stirred for 20 min. and filtered. The precipitate is dissolved in acetone, water slowly added, and the fine crystals collected. This yields 490 mg (86%) of title compound which showed: mp 178°-80° C.; [a] −42.1° (c=1.1 EtOH); Anal. (C H NO H O) C,H,N.

EXAMPLE 2

2'7-Disuccinyltaxol

A solution of 300 mg (0.35 mmole) of taxol, 500 mg (4.2 mmole) of succinic anhydride and 10 mg of DMAP in 4 mL of DMF is heated at 85° C. for 10 h (single spot by TLC using silica, chloroform/acetone, 9:1). With the use of the same procedure as for 2'-succinyltaxol above, the crude product is isolated, and chromatographed on 5 g of silica using toluene/10-50% acetone. This gave 300 mg (68%) of crystalline material: mp 180°-1° C.; [a] −30.1° (c=1.05, EtOH); Anal. (C H NO) C,H,N.

EXAMPLE 3

2'-Glutaryltaxol

With the use of a similar procedure as for 2'-succinyltaxol, 400 mg of taxol gives 480 mg (94%) of pure 2'-glutaryltaxol after recrystallization from chloroform/benzene: mp 156°-8° C.; Anal. (C H NO) C,H,N.

EXAMPLES 4 TO 7

Following the procedure of Example 1 except substituting for succinic anhydride the anhydride shown in column II of Table I, the product shown in column III is obtained:

TABLE I

| Example No. | Anhydride | Product |
|---|---|---|
| 4 | maleic | taxol-2'-OCOCHCHOCO$_2$H |
| 5 | 1,2-cyclohexane-dicarboxylic acid | taxol-2'-OCOC$_6$H$_{10}$CO$_2$H |
| 6 | 4-cyclohexene-1,2-dicarboxylic acid | taxol-2'-OCOC$_6$H$_8$CO$_2$H |
| 7 | phthalic | taxol-2'-OCOC$_6$H$_4$CO$_2$H |

EXAMPLE 8

2'-Succinyltaxol, Triethanolamine Salt

A methanolic solution of 2'-succinyltaxol of Example 1 is added to an aqueous solution of an equivalent amount of triethanolamine. After evaporation of the solvents, the gummy solid is dissolved in water and freeze-dried to yield the title compound. Anal. (C H N O 3H O) C,H,N.

EXAMPLES 9 TO 24

Following the procedure of Example 8, except for substituting triethanolamine the base shown in column II of Table II, the corresponding salt of the acid 4 is obtained:

TABLE II

| Example No. | Acid From Example No. | Base |
|---|---|---|
| 9 | 1 | $(CH_3)_3N$ |
| 10 | 1 | N methyl-N,-N-diethanolamine |
| 11 | 1 | N-methylglucamine |
| 12 | 1 | NaOH |
| 13 | 1 | $NH_3$ |
| 14 | 3 | $(C_2H_5)_3N$ |
| 15 | 3 | 1,6-diaminohexane |
| 16 | 3 | $(HOC_2H_4)_3N$ |
| 17 | 3 | NaOH |
| 18 | 3 | $C_6H_5CH_2NH_2$ |
| 19 | 3 | N-methylglucamine |
| 20 | 3 | N-methyl-N,-N-diethanolamine |
| 21 | 4 | 2-aminoethanol |
| 22 | 5 | $CH_3NH_2$ |
| 23 | 6 | $(HOC_2H_4)_3N$ |
| 24 | 7 | 1,5-diaminoheptane |

EXAMPLE 25

Aminoamide Derivative of 2'-Glutaryltaxol

To a well stirred solution of 4.00 g (4.13 mmole) of 2'-glutaryltaxol of Example 3 in 40 mL of acetonitrile is added 0.88 g (5.43 mmole) of carbonyldiimidazole, and the mixture heated to 45° for 5 minutes. After cooling to room temperature, a solution of 0.47 g (4.61 mmole) of 3-dimethylamino-1-propylamine in 3 mL of acetonitrile is added over a period of 20 minutes. After 30 minutes, the solvent is evaporated and the residue treated with 150 mL of water and 40 mL chloroform. The organic layer is washed five times with 150 mL of water, dried with K CO and evaporated. Recrystallization from methylene chloride/ethyl acetate yields 3.6 g (83%) of title compound. An additional 0.50 g (11%) of title compound can be recovered by the preparation of an oxalate salt and conversation back to the free base: mp 135°-7° C.; MS-FAB m/z 1052.4 (M +1, 100), calc. 1052.5; Anal. (C H N O H O) C,H,N.

The hydrochloride salt of the title compound is prepared by slow addition of 500 mg of the title compound dissolved in about 1 mL of warm EtOH, to 1 equivalent of HCl in 50 mL of water followed by freeze-drying: H-NMR (CDCl) 2.76 and 2.85 (d, J=4.9, HN (CH)) ppm; Anal. (C H ClN O 3H) C,H, Cl,N.

EXAMPLES 26 TO 43

Following the procedure of Example 25 except substituting for 3-dimethylamino-1-propylamine the reactant in column III of Table III and the acid derivative of taxol in column II, the product shown in column IV is obtained:

TABLE III

| Example No. | Taxol Acid From Example No. | Reactant | Product |
|---|---|---|---|
| 26 | 3 | $NH_2(CH_2)_2N(CH_3)_2$ | $RNH(CH_2)_2N(CH_3)_2$ <br> R = Taxol-2'-$OCO(CH_2)_3CO$— |
| 27 | 3 | $NH_2(CH_2)_2N(CH_2)_5$ | $RNH(CH_2)_2N(CH_2)_5$ |
| 28 | 3 | $NH_2(CH_2)_2N(C_2H_4)_2NCH_3$ | $RNH(CH_2)_2N(C_2H_4)_2NCH_3$ |
| 29 | 3 | $NH_2(CH_2)_2N(C_2H_4)_2S$ | $RNH(CH_2)_2N(C_2H_4)_2S$ |
| 30 | 3 | $NH_2(CH_2)_2NHCH_2C_6H_5$ | $RNH(CH_2)_2NHCH_2C_6H_5$ |
| 31 | 3 | $NH_2(CH_2)_2N(CH_2)_4$ | $RNH(CH_2)_2N(CH_2)_4$ |
| 32 | 3 | $HO(CH_2)_2N(CH_3)_2$ | $RO(CH_2)_2N(CH_3)_2$ |
| 33 | 3 | $HS(CH_2)_2N(CH_3)_2$ | $RS(CH_2)_2N(CH_3)_2$ |
| 34 | 3 | $HOCH_2CON(CH_3)_2$ | $ROCH_2CON(CH_3)_2$ |
| 35 | 3 | $HOCH_2CON(CH_3)CH_2CO_2Na$ | $ROCH_2CON(CH_3)CH_2CO_2H$ |
| 36 | 3 | $HOCH_2CON(CH_3)(CH_2)_2N(CH_3)_2$ | $ROCH_2CON(CH_3)(CH_2)_2N(CH_3)_2$ |
| 37 | 1 | $NH_2(CH_2)_2N(CH_3)_2$ | $RNH(CH_2)_2N(CH_3)_2$ <br> R = taxol-2'-$OCO(CH_2)_2CO$— |
| 38 | 1 | $HS(CH_2)_3N(C_2H_5)_2$ | $RS(CH_2)_3N(C_2H_5)_2$ |
| 39 | 1 | $HO(CH_2)_2N(CH_2)_4$ | $RO(CH_2)_2N(CH_2)_4$ |
| 40 | 1 | $HOCH_2CON(C_2H_5)_2$ | $ROCH_2CON(C_2H_5)$ |
| 41 | 4 | $NH_2(CH_2)_2N(CH_2C_6H_5)_2$ | $RNH(CH_2)_2N(CH_2C_6H_5)_2$ <br> R = taxol-2'-$OCOCHCHCO$— |
| 42 | 6 | $NH_2(CH_2)_2N(CH_3)_2$ | $RNH(CH_2)_2N(CH_3)_2$ <br> R = taxol-2'-$OCOC_6H_8CO$— |
| 43 | 7 | $NH_2(CH_2)_3N(C_2H_5)_2$ | $RNH(CH_2)_3N(C_2H_5)_2$ <br> R = taxol-2'-$OCOC_6H_4CO$— |

EXAMPLE 44

Methyl Iodide Quarternary Salt Of Aminoamide Derivative of 2'-Glutaryltaxol

To a solution of 1 mmole of aminoamide derivative of 2'-glutaryltaxol of Example 25 in 50 mL of acetonitrile there is added 10 mmole of methyl iodide and the mixture is refluxed for 24 hours. The solvent is evaporated, the residue taken up in methanol and the product is precipitated by slow addition of ethyl ether and filtered off.

TABLE IV

Analytical Data For Certain Exemplary Compounds

| Example No. | Calculated | | | | Found | | | |
|---|---|---|---|---|---|---|---|---|
| | C | H | N | Cl | C | H | N | Cl |
| 1 | 63.00 | 5.91 | 1.44 | | 63.20 | 5.82 | 1.43 | |
| 2 | 62.71 | 5.56 | 1.33 | | 62.57 | 3.65 | 1.30 | |
| 3. | 64.52 | 5.93 | 1.45 | | 64.64 | 5.97 | 1.42 | |
| 8 | 59.22 | 6.64 | 2.42 | | 59.22 | 6.59 | 2.40 | |
| 11 | 57.04 | 6.60 | 2.29 | | 57.19 | 6.63 | 2.28 | |
| 16 | 61.38 | 6.58 | 2.47 | | 61.00 | 6.55 | 2.45 | |
| 17 | 59.80 | 5.99 | 1.43 | | 59.60 | 5.85 | 1.36 | |
| 26 | 63.97 | 6.69 | 3.93 | | 64.15 | 6.68 | 3.83 | |
| 26.HCl | 59.91 | 6.70 | 3.58 | 3.10 | 59.98 | 6.65 | 3.69 | 3.16 |

TABLE V

$^1$H NMR Data For Various Taxol Derivatives In Deuteriochloroform

| Protons On: | 1 | 2 | 3 | 26 |
|---|---|---|---|---|
| C-2 | 5.68 (d, 7) | 5.67 (d, 7) | 5.72 (d, 7) | 5.68 (d, 7.1) |
| C-3 | 3.80 (d, 6.9) | 3.91 (d, 7) | 3.81 (d, 6.9) | 3.80 (d, 6.8) |
| C-5 | 4.97 (d, 7.4) | 4.97 (d, 9.5) | 4.99 (d, 7.4) | 4.98 (dd, 2, 9.6) |
| C-7 | 4.44 (dd, 7, 12) | 5.64 (m) | 4.40 (dd, 7, 11) | 4.44 (m) |
| C-10 | 6.29 (s) | 6.21 (s) | 6.32 (d) | 6.30 (s) |
| C-13 | 6.24 (t, 9) | 6.18 (t, 9) | 6.22 (t, 9.6) | 6.22 (t, 7.2) |
| C-16, 17 | 1.22, 1.13 (s) | 1.19, 1.15 (s) | 1.22, 1.15 (s) | 1.26, 1.14 (s) |
| C-18 | 1.91 (s) | 1.95 (s) | 1.95 (s) | 1.94 (s) |
| C-19 | 1.67 (s) | 1.79 (s) | 1.69 (s) | 1.68 (s) |
| C-20 | 4.33 (d, 8.4) | 4.32 (d, 8.3) | 4.32 (d, 8.4) | 4.31 (d, 8.6) |
| C-20 | 4.20 (d, 8.4) | 4.18 (d, 8.3) | 4.25 (d, 8.4) | 4.20 (d, 8.6) |
| C-2' | 5.53 (d, 3.4) | 5.58 (d, 3.7) | 5.47 (d, 3.1) | 5.45 (d, 3.9) |
| C-3' | 5.98 (dd, 3.4, 9) | 5.95 (dd, 3.6, 9) | 5.98 (m) | 5.96 (dd, 4, 8.8) |
| N—H | 7.05 (d, 9) | 7.08 (d, 9.2) | 7.12 (d, 9) | 7.03 (bd) |
| OAc | 2.44 | 2.38 | 2.33 | 2.45 |
|  | 2.21 | 2.13 | 2.22 | 2.23 |
| R$_1$ or R$_2$ | 2.61 (t, 7) | 2.5-2.8 (m) | 2.3-2.6 (m) | 2.17 (s, N—Me) |
|  | 2.69 (t, 7) |  |  |  |

Solubility and Antineoplastic Activity

One of the important objectives of this invention is the synthesis of compounds with improved aqueous solubility, since taxol is essentially insoluble in water. Although the mono and bis succinates of Examples 1 and 2 are not water soluble, their sodium salts are soluble to the extent of about 0.1% and 0.3%, respectively. In each case the sodium salt has improved antitumor activity as compared to the free acid. It is noted that the 2',7-bis compound of Example 2 and its sodium salt are, in each case, considerably less active than the corresponding 2'-mono derivative of Example 1 and its salts.

Since salts prepared with different counter ions often have substantially different properties, compounds of Example 8 and Example 11 were made from monosuccinate of Example 1 using triethanolamine and N-methylglucamine, respectively. Both of these salts have greatly improved aqueous solubility, forming normal solutions up to about 1% concentration. Above this level, although still soluble, the solutions were not clear and became very viscous resembling concentrated soap solutions. Compounds of Examples 8 and 11 were both much more active than the compound of Example 12, with the triethanolamine salt of Example 8 being especially active and potent. Another conveniently prepared acid derivative of taxol was the 2'-monoglutarate of Example 3. Both the sodium salt, i.e., Example 17, and the triethanolamine salt, i.e., Example 16, are very active and potent and they generally seem to have improved biological properties as compared to the corresponding succinates of Examples 12 and 8.

The glutarate series is also preferred because of the higher yield obtained in the synthesis of 2'-O-glutaryl-taxol of Example 3.

Another approach to make basic derivatives is based on the concept of taking an existing hydrolysable derivative and further modifying it to form a derivative that allows for stepwise hydrolysis. Thus, coupling 2'-glutaryl-taxol with 2-(dimethylamino)-1-propylamine, using N,H-carbonyldiimidazole gives in excellent yield (88% from taxol) the amino amide of Example 25. In addition to showing good solubility, is the hydrochloride salt, i.e., up to about 1%, the compound is extremely potent and active. At 10 mg/Kg, in the B16 screen, the HCl-salt of Example 26 had a T/C of 352 with 5 out of 10 cures. In the MX-1 breast xenograft (3MBG5) assay, this derivative gave the remarkable values of −100 (complete tumor disappearance) at does of 40 and 20 mg/Kg, with all live animals being tumor free. The in vivo screening results for exemplary compounds synthesized are shown in Table VI.

TABLE VI

Antitumor Activity in the B16 Melanoma System[a]

| Compound of Example No. | Dose Per INJ[b] mg/Kg | Survivors Day 4[c] | WT Diff, g (T − C)[c] | % T/C[c] (cures) |
|---|---|---|---|---|
| Taxol | 40 | 10/10 | −1.2 | TOXIC |
|  | 20 | 10/10 | −0 | 96 |
|  | 10 | 10/10 | 0 | 139 |
|  | 5 | 10/10 | −0.2 | 175 |
| 1 | 40 | 10/10 | 0 | 185 (2) |
|  | 20 | 10/10 | 0 | 154 |
|  | 10 | 10/10 | 0.4 | 159 (1) |
|  | 5 | 10/10 | 0.4 | 154 |
|  | 2.5 | 10/10 | 0 | 119 |
| 2 | 44 | 10/10 | 0 | 114 |
|  | 22 | 10/10 | 0.3 | 105 |
|  | 11 | 10/10 | 0.1 | 124 |
|  | 5.5 | 10/10 | −0.3 | 113 |
|  | 2.75 | 10/10 | −0.3 | 109 |
| 2, Na-Salt | 44 | 10/10 | 0 | 166 |
|  | 22 | 10/10 | 0 | 109 |
|  | 11 | 10/10 | −0.1 | 149 |
|  | 5.5 | 10/10 | 0.6 | 114 |
|  | 2.75 | 10/10 | 0.6 | 120 |
| 8 | 54 | 10/10 | −0.4 | TOXIC |
|  | 7 | 10/10 | −0.8 | 314 (3) |
|  | 13.5 | 10/10 | 0.6 | 264 (1) |
|  | 6.75 | 10/10 | 0 | 230 (1) |
| 11 | 50 | 10/10 | −0.6 | 241 |
|  | 25 | 10/10 | 0.3 | 176 |
|  | 12.5 | 10/10 | 0.3 | 134 |
|  | 6.25 | 10/10 | −0.2 | 125 |
| 12 | 40 | 10/10 | 0.6 | 218 (2) |
|  | 20 | 10/10 | −0.2 | 201 |
|  | 10 | 10/10 | 0.6 | 183 |
|  | 5 | 10/10 | 0 | 166 |
|  | 2.5 | 10/10 | 0.4 | 159 (1) |
|  | 40 | 10/10 | −1.3 | 177 |
|  | 20 | 10/10 | −0.4 | 160 |
|  | 10 | 10/10 | 0.4 | 160 (1) |
|  | 5 | 10/10 | −0.1 | 131 |
|  | 2.5 | 10/10 | 0 | 125 |
|  | 1.25 | 10/10 | 0.1 | 111 |
| 16 | 53 | 8/8 | 0.4 | 300 (1) |
|  | 26.5 | 8/8 | 0.4 | 239 (2) |
|  | 13.25 | 8/8 | 0.4 | 291 |
|  | 6.63 | 8/8 | 0.4 | 207 |
| 17 | 49 | 7/7 | 0.4 | 339 |

TABLE VI-continued
Antitumor Activity in the B16 Melanoma System[a]

| Compound of Example No. | Dose Per INJ[b] mg/Kg | Survivors Day 4[c] | WT Diff, g (T − C)[c] | % T/C[c] (cures) |
| --- | --- | --- | --- | --- |
| | 24.5 | 7/7 | 1.5 | 225 |
| | 12.25 | 8/8 | 0.6 | 192 |
| | 6.13 | 8/8 | 0.4 | 159 |
| 25, HCl-Salt | 20 | 10/10 | 0 | 352 (6) |
| | 10 | 10/10 | −0.1 | 352 (5) |
| | 5 | 10/10 | 0.1 | 188 |
| | 2.5 | 10/10 | −0.1 | 129 |
| | 1.2 | 10/10 | −0.1 | 123 |
| 25, HCl-Salt | 40 | 5/6 | −5.9 | −100 (5) |
| Human MX-1 | 20 | 5/6 | 0.3 | −100 (5) |
| Mammary | 10 | 6/6 | −2.2 | 1 |
| Tumor | 5 | 6/6 | 0.1 | 1 |
| Xenograft | 2.5 | 6/6 | −0.6 | 22 |

[a]Screening was carried out under the auspices of the National Cancer Institute. For detailed explanations of procedures and data, see Instruction 14, Screening Data Summary Interpretation and Outline of Current Screen, Drug Evaluation Branch, Developmental Therapeutics Program, Division of Cancer Treatment, National Cancer Institute, Bethesda, Maryland 20892.
[b]Q01D × 09. Single dose for 9 days; given in milligrams per kilogram body weight per injection.
[c]Abbreviations: survivors day 4, live animals on the fourth day of testing/total animal; wt diff, g (T − C), the difference in body weight in grams between test and control animals; % T/C, the median lifetime of test animals divided by the median lifetime of control animals, times 100; for the solid tumor system % T/C is 100 × (change in treated tumor wt 1 day 11 − day 0)/change in control tumor wt.) if the tumor grows or 100 × (change in treated tumor wt./initial treated tumor wt.) if the tumor regresses; cures, number of live animals on the last day of evaluation for the B16 melanoma system (day 60) or number of animals without measurable tumor on day 11 for the MX-1 mammary tumor system.

The data presented herein clearly supports the therapeutic utility of the water soluble derivatives of the present invention for treating cancer, wherein said cancer is sensitive to said treatment.

A pharmaceutical composition comprising antineoplastically effective amount of water soluble derivative of taxol as an active ingredient is easily prepared by standard procedures well known in the art, with pharmaceutically acceptable non-toxic sterile carriers, if necessary. Such preparations could be administered orally or in injectable form to a subject afflicted with cancer, for the treatment thereof, wherein said cancer is sensitive to said treatment.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:
1. A method of treating cancer sensitive to treatment with the compound set forth below, comprising administering to a subject afflicted with said cancer, an effective amount of the water soluble derivative of the compound of the following formula to cause regression of said cancer:

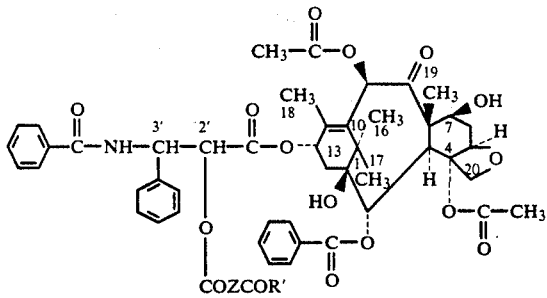

Wherein:
Z = ethylene, propylene, CHCH, 1,2-cyclohexane, 1,2-phenylene,
$R^1$ = OH base, $NR^2R^3$, $OR^3$, $SR^3$, $OCH_2CONR^4R^5$, OH
$R^2$ = hydrogen, methyl
$R^3$ = $(CH_2)_n NR^6R^7$; $(CH_2)_n NR^{\oplus 6}R^7R^8 X^{\ominus}$
n = 1 to 3
$R^4$ = hydrogen, lower alkyl containing 1 to 4 carbons
$R^5$ = hydrogen, lower alkyl containing 1 to 4 carbons, benzyl, hydroxyethyl, $CH_2CO_2H$, dimethylaminoethyl
$R^6R^7$ = lower alkyl containing 1 or 2 carbons, benzyl or $R^6$ and $R^7$ together with the nitrogen atom of $NR^6R^7$ form the following rings

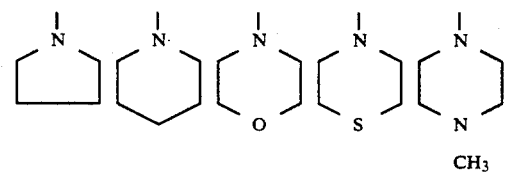

$R^8$ = lower alkyl containing 1 or 2 carbons, benzyl
$X^{\ominus}$ = halide
base = $NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

2. The method of claim 1 wherein said water soluble derivative is 2'-succinyl-taxol.
3. The method of claim 1 wherein said water soluble derivative is 2'-succinyl taxol triethanolamine.
4. The method of claim 1 wherein said water soluble derivative is 2'-glutaryl-taxol.
5. The method of claim 1 wherein said water soluble derivative is 2'-glutaryl-taxol triethanolamine salt.
6. The method of claim 1 wherein said water soluble derivative is 2'-O-ester with N-(dimethylaminoethyl) glutamide.
7. The method of claim 1 wherein said water soluble derivative is 2'-O-ester with N-(dimethylaminoethyl) glutamide hydrochloride salt.

* * * * *